(12) United States Patent
Holtermann

(10) Patent No.: US 6,409,710 B1
(45) Date of Patent: *Jun. 25, 2002

(54) COUPLING FOR OSTOMY APPLIANCE, AND OSTOMY APPLIANCE COMPRISING SUCH A COUPLING

(75) Inventor: Henri Holtermann, Saint-Jean-de-Luz (FR)

(73) Assignee: B. Braun Biotrol, Boulogne Billancourt (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/265,755

(22) Filed: Mar. 10, 1999

(30) Foreign Application Priority Data

Mar. 12, 1998 (FR) .............................. 98 03061

(51) Int. Cl.$^7$ .................................... A61F 5/44
(52) U.S. Cl. ..................... 604/342; 604/338; 604/332
(58) Field of Search ................. 604/327, 331, 604/338, 332, 337, 339, 341, 342, 317

(56) References Cited

U.S. PATENT DOCUMENTS

| | | | |
|---|---|---|---|
| 2,656,838 A | * | 10/1953 | McConnell |
| 5,180,377 A | * | 1/1993 | Holtermann ................ 604/342 |
| 5,322,523 A | * | 6/1994 | Olsen |
| 5,520,670 A | * | 5/1996 | Blum |
| 5,647,861 A | * | 7/1997 | Steer et al. ................ 604/342 |

FOREIGN PATENT DOCUMENTS

| | | | |
|---|---|---|---|
| DE | 12 66 929 | | 4/1968 |
| EP | 0 433 102 | | 6/1991 |
| EP | 799 608 | * | 3/1997 |
| EP | 0 799 608 | | 10/1997 |
| FR | 1 156 435 | | 5/1958 |

* cited by examiner

Primary Examiner—Brian L. Casler
Assistant Examiner—LoAn H. Thanh
(74) Attorney, Agent, or Firm—Alston & Bird LLP

(57) ABSTRACT

A coupling for an ostomy appliance, comprises two elements (10, 20), each including a base (11, 21), equipped with a central opening, and a tubular joining piece (12, 22) surrounding the opening. The joining piece (12) of the first element (10) comprises, on its internal face, an elastically deformable annular lip (18) whose free end (19) is directed towards the plane of the base (11) of the element. The joining piece (22) of the second element (20) includes, on its external face, means for axial retention (44) of the free end of this lip. This coupling includes a locking member (43), and the means for axial retention of the free end of the annular lip occupy a sector of the circumference of the joining piece of the second element, of which the midpoint is situated diametrically opposite the locking member under conditions of assembly and disassembly of the two elements of this coupling.

21 Claims, 4 Drawing Sheets

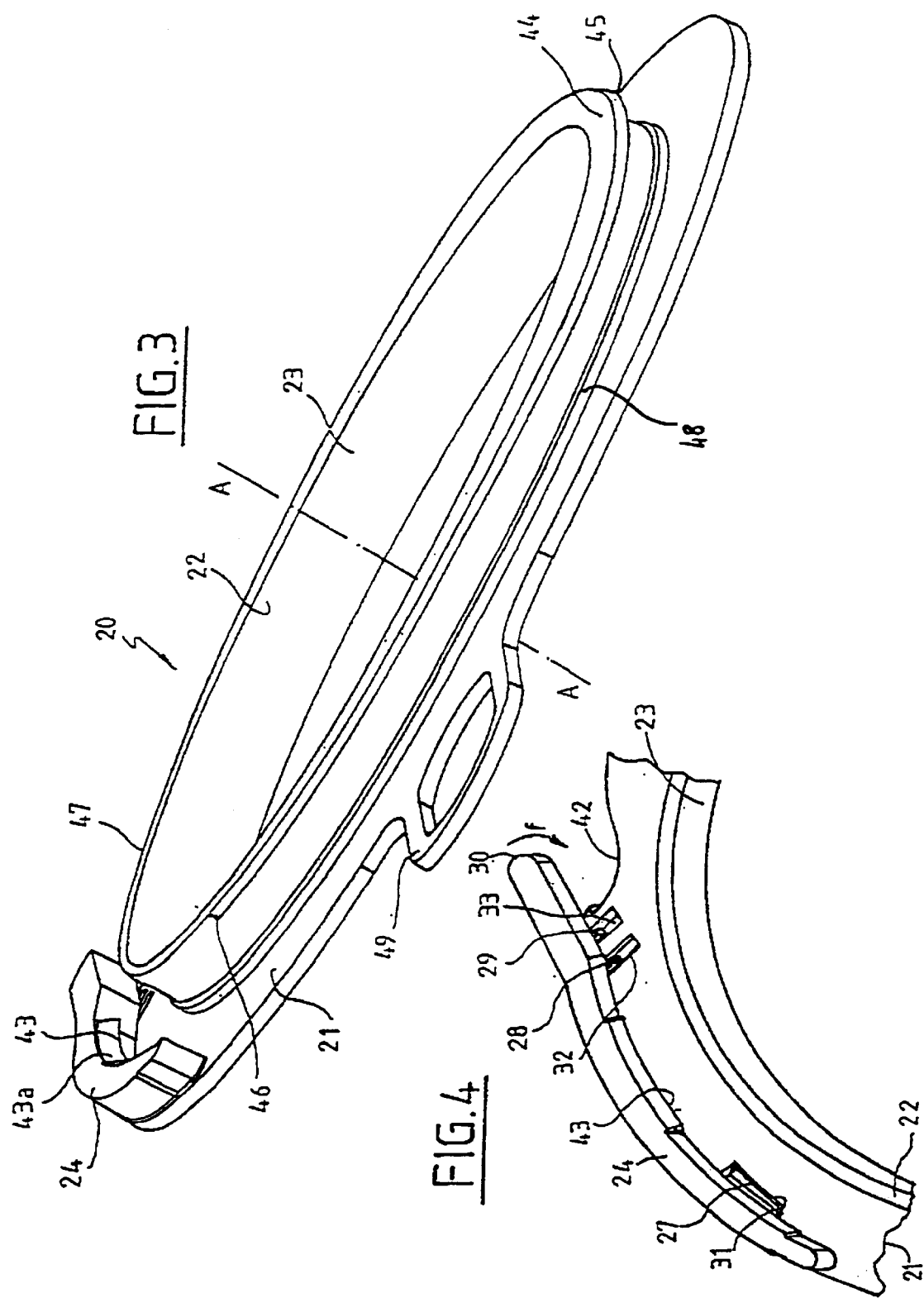

COUPLING FOR OSTOMY APPLIANCE, AND OSTOMY APPLIANCE COMPRISING SUCH A COUPLING

The present invention relates to a coupling which can form part of the structure of an ostomy appliance, and also to an ostomy appliance comprising such a coupling.

A great many appliances have already been proposed for the collection of bodily matter (faeces, urine, etc.) in persons who have undergone surgery of the gastrointestinal tract, of the ileostomy or colostomy type, or surgery of the urinary tract, of the urostomy type, or surgery necessitating the drainage of wounds or of intra-abdominal cavities, of the peritoneal or sub-peritoneal drainage type. Among these appliances, a basic distinction is made between:

appliances referred to as "one-piece" appliances because they consist of a collecting bag which comprises a skin protector provided with a pressure-sensitive adhesive and which is intended to be fixed on the user's skin by way of this skin protector alone, and appliances referred to as "two-piece" appliances which comprise a frontal sheet or "bag holder" intended to be fixed on the user's skin and provided, for this purpose, with an adhesive pad, and a collecting bag which can be removably attached to this frontal sheet by means of a joining piece with which it is provided.

The ostomy appliances of the "two-piece" type have to satisfy certain conditions, some of which are inherently contradictory. Thus, although it is essential that the fixing of the collecting bag on the bag holder is secure in such a way as to prevent any inadvertent separation of this bag, particularly under the effect of the stresses exerted by the weight of the bodily matter with which it fills, and moreover that it guarantees perfect leaktightness of the appliance in relation to this matter, it is also desirable that the ostomy patients —who are often elderly subjects can, after a period of training by nursing staff, put the bag holder in place themselves, on the one hand, and, on the other hand, place the collecting bags on the bag holder, and this means that the manoeuvres for joining and disconnecting the bag and bag holder must be as simple and straightforward as possible.

To this end, two-piece appliances have been proposed, in a great many embodiments, in which the collecting bag and the bag holder are joined together by force-fitting, under the effect of a pressure applied by the patient, a joining piece, which is equipped with an annular sealing lip and is situated preferably on the bag, into a channel which has a shape and dimensions matching those of the said joining piece and which is formed by two other joining pieces situated preferably on the bag holder. These appliances, described in GB-A-1 571 657 and EP-A-0 171 255, for example, have the advantage that a single engagement operation ensures, on the one hand, the attachment of the bag and the bag holder and, on the other hand, the leaktightness of the appliance. However, in practice, to obtain satisfactory results, these appliances demand that the patient exert a considerable pressure on the bag, when placing it on the bag holder, and, consequently, on the area surrounding the stoma, which is generally very sensitive, sometimes very painful, so that the use of these appliances is not really satisfactory.

In an attempt to solve this problem, it has been proposed in GB-A-2 237 993 and GB-A-2 237 995 to improve this type of appliance by configuring the joining pieces of the collecting bag and of the bag holder in such a way that they are joined together, no longer by force-fitting, but by the joining piece of the bag snapping between the two joining pieces of the bag holder, and in such a way that their attachment is ensured by means of the end of the annular sealing lip of the joining piece of the bag pressing against a rib, likewise annular, situated on one of the joining pieces of the bag holder. Although these appliances do indeed allow the bag and the bag holder to be joined together without exerting pressure on the area surrounding the stoma, they nevertheless pose another problem, namely that in order to disconnect them, they require that a considerable pulling force be applied on the said bag, which, once again, can cause pain on account of the sensitivity of the area surrounding the stoma, and which can also cause partial or total tearing of the bag holder from the patient's skin, rendering it unsuitable for further use.

Two-piece appliances have also been proposed in which the device for joining the collecting bag and the bag holder together comprises, on the one hand, two joining pieces, one of which is situated on the bag while the other is fixed on the bag holder and which, when they are brought into contact with one another, are intended to ensure the leaktightness of the appliance by virtue of the presence of a sealing lip or sealing joint or by virtue of the matching nature of their shapes and/or their dimensions, and, on the other hand, a member of the circular ring type which is generally connected to one of these two joining pieces and which, by different mechanisms (cam effect, clamping effect, etc.), ensures the attachment of the bag on the bag holder in such a way that these can be joined together and disconnected by means of applying moderate, if any, forces of pressure in one case and of traction in the other, on the bag. Such appliances are described in EP-A-0 255 310 and in WO-A-91/01118, for example.

The appliances of this latter type are not totally satisfactory either to the extent that, although belonging to the two-piece appliance type, they in fact comprise at least three elements for joining the collecting bag to the bag holder, a fact which significantly complicates their realization, both in terms of the manufacture of the various components from which they are made up and the assembly of these components, and substantially increases their production cost, whereas the long-term use of appliances by ostomy patients dictates that these appliances be relatively inexpensive.

Consequently, a general object of the invention is to make available an ostomy appliance in which the device for joining together and disconnecting the collecting bag and the bag holder is made up of only two elements, in such a way as to have a relatively low production cost, while at the same time satisfying all the conditions demanded of such an appliance, and, especially, ease of use, ease of handling, security of the attachment of the bag on the bag holder and leaktightness in relation to the bodily matter, and which not only permits positioning of the bag on the bag holder without applying pressure in the area surrounding the stoma, but also permits removal of this bag without the need to exert considerable pulling force.

It is also an object of the invention to make available such an appliance which, once the collecting bag and the bag holder have been joined together, allows the patient to modify the position of the bag in relation to the bag holder in a simple way and without risk, for example in order to adapt the orientation of the bag as a function of his/her activities or to make it easier to empty.

According to the invention, these objects are achieved by a coupling which can form part of the structure of an ostomy appliance and which comprises two elements which can be joined together removably, each including a base, equipped with a central opening, and a tubular joining piece surrounding the said opening, in which the joining piece of the first element comprises, on its internal face, an elastically deformable annular lip whose free end is directed towards the plane of the base of the said element, while the joining piece of the second element includes, on its external face, means for axial retention of the free end of this lip, which coupling is characterized in that it includes a locking member, and in that the means for axial retention of the free end of the annular lip occupy a sector of the circumference of the joining piece of the second element, of which the midpoint is situated diametrically opposite the said locking member under conditions of assembly and disassembly of the two elements of this coupling.

Thus, to join the two elements of the coupling together, the user, after ensuring that the locking member is in the unlocked position, begins by positioning the annular lip of the first element so that it bears on the means for axial retention of the second element in the zone diametrically opposite the locking member. He then pivots one element relative to the other until the joining pieces of the two elements are fully engaged with one another. It then suffices for him to lock the locking member so as to secure the two elements of the coupling. This joining together does not therefore require the application of any pressure.

To disconnect the two elements of the coupling, it suffices to perform the opposite procedure: to unlock the locking member, move the two elements of the coupling away from each other at right angles to the locking member in such a way as to pivot one of the elements of the coupling in relation to the other one, with the annular lip remaining bearing on the means for retention in the zone diametrically opposite the locking member; thus, with the pivoting, the lip can finally be disengaged completely by the simple effect of geometry and, consequently, without the need to exert any pulling forces.

According to an advantageous arrangement of the coupling according to the invention, the means for axial retention of the free end of the annular lip occupy a sector of the circumference of the joining piece of the second element corresponding to an angle of between about 180 and 320° depending on the diameter of this joining piece, which is itself advantageously between about 25 and 100 mm. Thus, in the case of a joining piece having a diameter less than or substantially equal to 50 mm, the means for axial retention of the end of the annular lip will preferably occupy an angular sector of between 180 and 275°, whereas in the case of a joining piece of greater diameter, they will preferably extend over an angular sector of between 240 and 320°.

According to a preferred arrangement of the coupling according to the invention, the means for axial retention of the free end of the annular lip consist of a flange which extends radially, from the external face of the joining piece of the second element, outwards from this joining piece.

In a particularly preferred manner, this flange is a diminishing flange whose width is at its maximum at the midpoint of the sector which it occupies and decreases progressively in the direction of the ends of this sector.

To guarantee the locking of the two elements of the coupling, the latter advantageously comprises means for immobilizing the locking member in the locked condition.

According to another preferred arrangement of the coupling according to the invention, with the locking member being joined to one of the two elements, it is intended to cooperate, in response to the activation of a control mechanism joined to the same element as itself, with a bearing surface which is formed on the joining piece of the other of the two elements of this coupling.

According to a first preferred embodiment of the coupling according to the invention, the locking member and the control mechanism are joined to the second element of this coupling, and the locking member is intended to cooperate with a bearing surface which extends radially, from the external face of the joining piece of the first element, outwards from this joining piece.

According to an advantageous feature of this first preferred embodiment, the bearing surface intended to cooperate with the locking member is formed by the face, situated opposite the base of the first element, of a rib with bevelled faces projecting from the external face of the joining piece of this first element.

In a preferred manner, the rib with bevelled faces projecting from the external face of the joining piece of the first element extends over the entire circumference of this joining piece. Thus, when the ostomy appliance is in the condition of use, the locking of the two elements of the coupling is ensured irrespective of the position of the collecting bag in relation to the bag holder, so that the patient can modify this position, as he/she wishes, by rotating the said bag on the bag holder, without any risk of causing the said elements to unlock.

According to another advantageous feature of this first preferred embodiment, the locking member is in one piece with the control mechanism and consists of at least one rib with bevelled faces, of which one of the faces matches the face of the rib of the joining piece of the first element intended to serve as a bearing surface, and which projects from the face of the said control mechanism situated opposite the joining piece of the second element.

In a preferred manner, the control mechanism comprises an arm which is mounted so as to pivot about an axis formed by a pin with which it is provided, and which is engaged in an orifice formed in the base of the second element.

In this case, the second element advantageously comprises means for maintaining and guiding this arm in a plane parallel to that of its base.

These means for maintaining and guiding the arm advantageously comprise at least one stud projecting from that face of this arm situated opposite the base of the second element, having a free return end which determines a bearing face and which is adapted to pass through an oblong slot formed in the base of the second element, so that the said bearing face slides on a face of the said base situated on the side opposite the said arm.

In this case too, the arm advantageously includes, on its face situated opposite the base of the second element, at least one projecting piece adapted to cooperate with a nose formed on the external edge of this same base in order to ensure immobilization of the locking member in the locked condition.

According to yet another advantageous feature of this first preferred embodiment, the second element of the coupling moreover includes means which are able to limit the radial displacement of the bottom of the annular lip in the direction of the joining piece of the first element when the two elements of this coupling are joined together.

According to another preferred embodiment of the coupling according to the invention, the locking member is joined to the first element of this coupling and is intended to cooperate, in response to the activation of a control mechanism also joined to the said first element, with a bearing surface which extends radially, from the external face of the joining piece of the second element, inwards from this joining piece.

According to an advantageous feature of this preferred embodiment, the bearing surface intended to cooperate with the locking member is formed by the wall, situated opposite the base of the second element, of a recess formed in the thickness of the joining piece of this second element.

In a preferred manner, the recess formed in the thickness of the joining piece of the second element extends over the entire circumference of this joining piece. However, given that, in this embodiment, the locking member is joined to the first element of the coupling while the means for axial retention of the end of the annular lip of this first element are situated on the second element of this coupling, it is advantageous to provide for the presence, on the base of the second element, of two stops which are able to limit the rotation of one element relative to the other when these elements are joined together, in such a way as to prevent the locking member from being brought into cooperation with a portion of this recess which would be situated in the angular sector occupied by the said means for axial retention, thereby creating an area in which the joining pieces of the two elements of the coupling would at one and the same time be without means able to ensure their locking and without means able to axially retain the free end of the annular lip, and presenting an angular extension sufficient to cause inadvertent disconnection of these two elements.

According to another advantageous feature of this preferred embodiment, the locking member is in one piece with the activating mechanism and consists of a rod which is placed in a cylindrical opening passing through the joining piece of the first element, one end of which can be lodged in the recess formed in the thickness of the joining piece of the second element while its other end is integral with the activating mechanism.

In a preferred manner, this rod is threaded over all or part of its length and the activating mechanism is formed by a knurled wheel or the like which is able to permit its displacement by rotation in the cylindrical opening in which it is placed.

The invention also relates to an ostomy appliance, such as an appliance for ileostomy, colostomy or urostomy, or for post-surgical drainage of intra-abdominal spaces, of the peritoneal or sub-peritoneal drainage type, which appliance comprises a bag holder intended to be fixed around an artificial opening in the body of a user, and a bag which collects the bodily matter and which can be joined in a removable manner to the said bag holder, characterized in that it comprises a coupling as defined hereinabove.

In addition to the above features, the invention also includes other features which will become evident from the following description which is given by way of example and in which reference is made to the attached drawings, in which:

FIG. 1b is a cross section, on a larger scale, along the line 1b—1b in FIG. 1a;

FIG. 3 is a perspective view of an element in FIG. 2, on a larger scale than that of FIG. 2;

FIG. 4 is a perspective view of a detail of the element in FIG. 2, on a larger scale than in FIG. 2;

It must be clearly understood, however, that these drawings and the corresponding parts of the description are given solely as an illustration of the subject of the invention and do not in any way constitute a limitation thereof.

In the drawings, those elements of the various embodiments which are equivalent have been given identical reference numbers.

Reference will first be made to FIGS. 1 to 8 which show a first embodiment of a coupling for an ostomy appliance according to the invention, which comprises two elements 10 and 20 which are intended to be fixed on the collecting bag and on the bag holder, respectively, of such an appliance and which are designed to be joined together removably, as will be explained hereinafter.

Figure 1A:
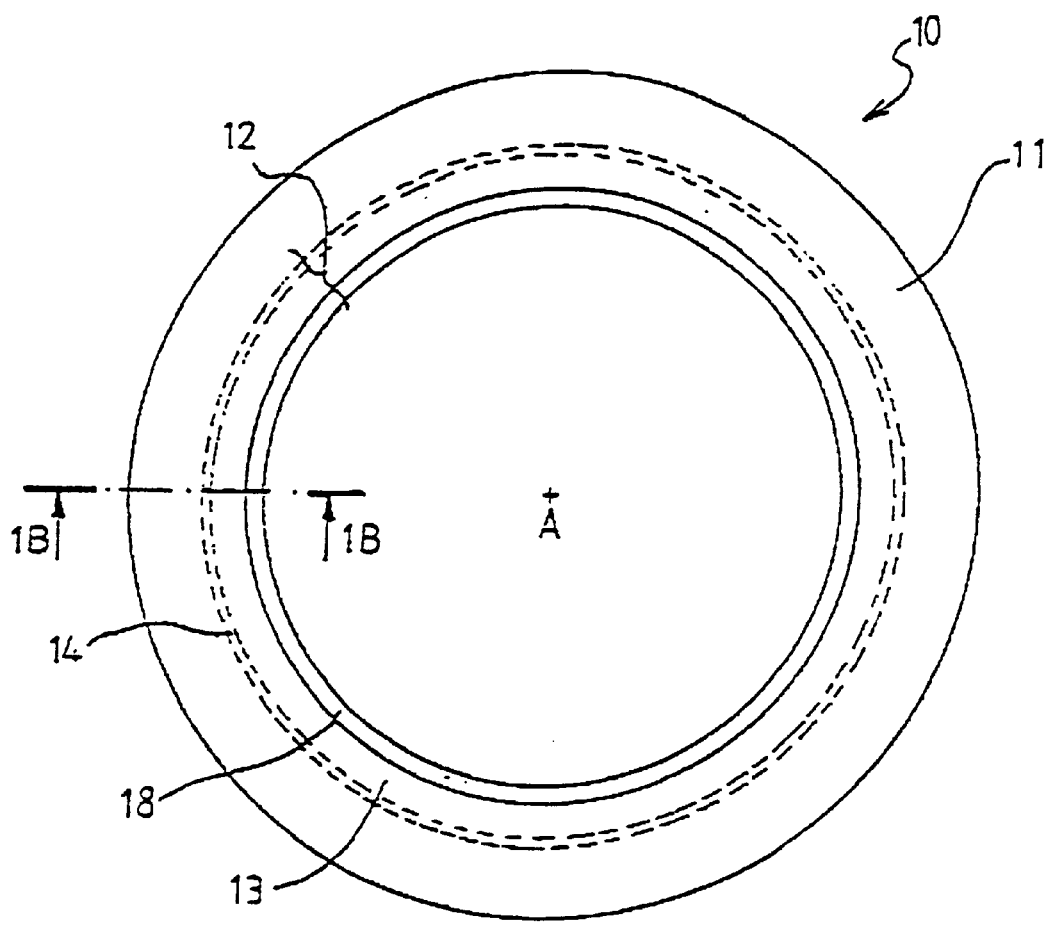
FIG. 1a is a plan view of the first element of a coupling for an ostomy appliance according to the invention, for a first embodiment of this coupling.
Figure 1B:
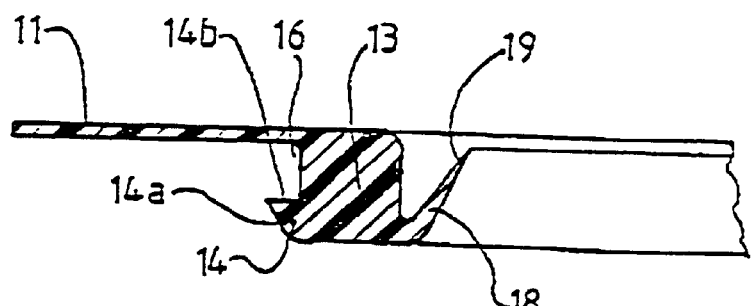

The first element of the coupling—which is represented in FIGS. 1a and 1b—or element 10 comprises an annular base 11, of axis of revolution A, on the internal edge of which a tubular joining piece 12 is built. This joining piece comprises a cylindrical wall 13 which is perpendicular to the base 11, and of the same axis as the latter, and which includes, projecting from its external face, an annular rib 14 with two bevelled faces 14a and 14b, this rib delimiting, together with the said base, an annular groove 16. The cylindrical wall 13 furthermore includes, projecting from its internal face, an elastically deformable lip 18 which extends obliquely from the free end of this wall in the direction of the plane of the base 11 and which is intended to ensure the leaktightness of the coupling with respect to the collected bodily matter in the condition of use of the ostomy appliance.

Figure 6:
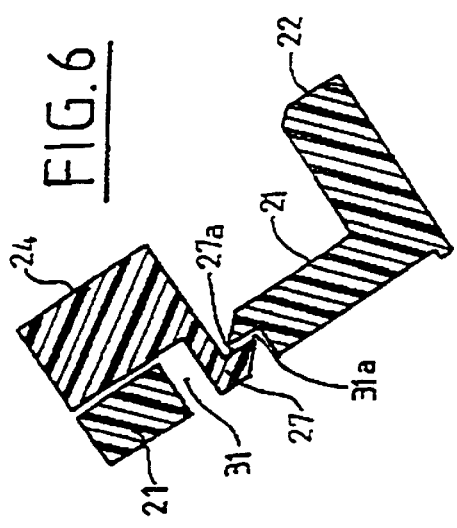
FIG. 6 is a cross section, on a larger scale, along the line 6—6 in FIG. 2.
Figure 7:
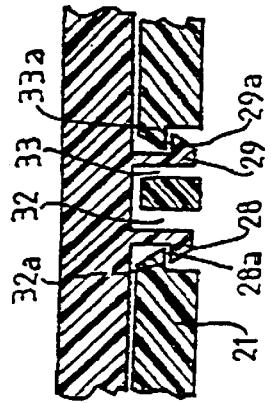
FIG. 7 is a cross section, on a larger scale, along the line 7—7 in FIG. 2.
Figure 8:
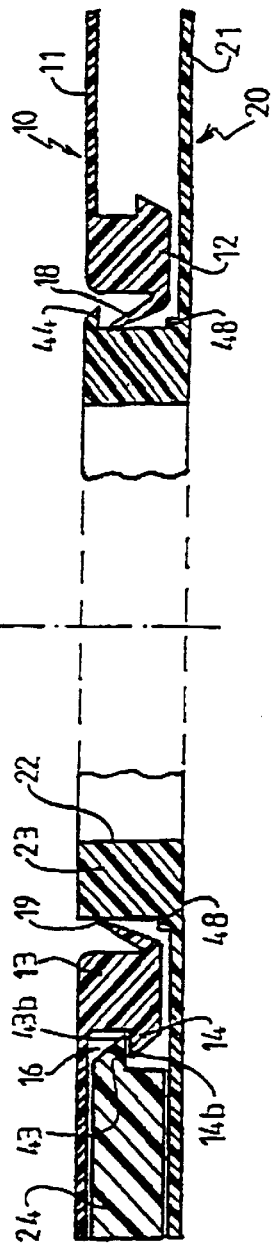
FIG. 8 is a diagrammatic cross section along the line 8—8 in FIG. 2, after joining of the element in FIG. 1 and of the element in FIG. 2, on a larger scale than those of these Figures.

The second element of the coupling or element 20—which for its part is represented in FIGS. 2 to 7—also comprises an annular base 21, of axis of revolution B, which bears, on its internal edge, a tubular joining piece 22 comprising a cylindrical wall 23 perpendicular to the said base and coaxial with the latter. This joining piece is intended to be engaged in the joining piece 12 of the element 10, when joining the two elements 10 and 20 of the coupling together, and is designed in such a way that, during this engagement, the free end 19 of the annular lip 18 of the joining piece 12 will, as can be seen in FIG. 8, come to bear against the external face of the said cylindrical wall 23 and can thereby fulfil its function as sealing member. For this reason, the external diameter of the cylindrical wall 23 of the joining piece 22 is chosen so as to be slightly smaller than the internal diameter of the cylindrical wall 13 of the joining piece 12, while being slightly larger than the internal diameter which the annular lip 18 of the joining piece 12 has in the area of its free end 19, when the two joining pieces 12 and 22 are not engaged.

Figure 5:
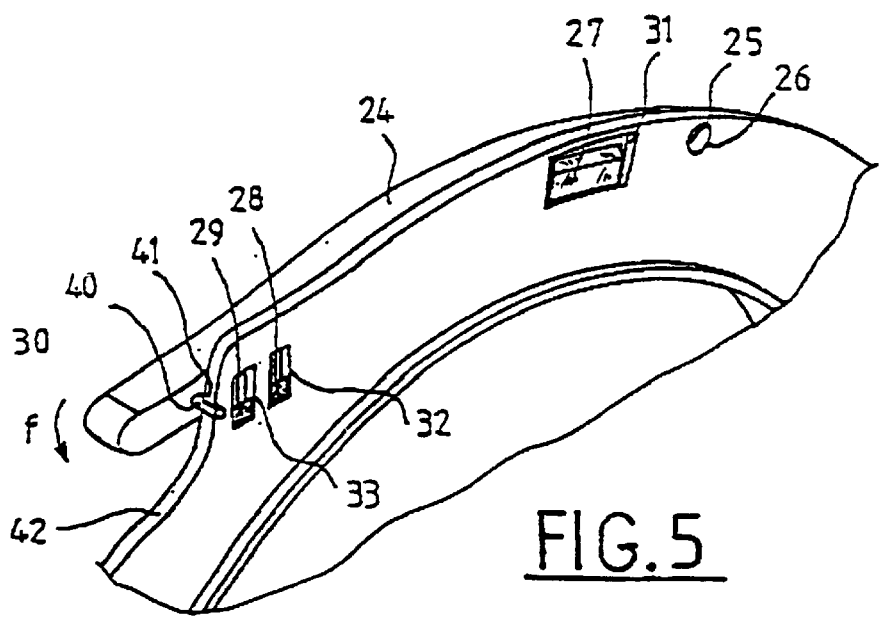
FIG. 5 is a rear perspective view of the detail from FIG. 4.

The element 20 is equipped with an arm 24 of a generally curved shape and of rectangular cross section which—as can be seen in FIG. 5—is mounted so as to pivot, on a pin 25 with which it is provided, in an orifice 26 formed in the base 21 at a short distance from the external edge of the latter, and whose activation is able to ensure, by way of a rib with which it is provided and which will be described hereinafter, the locking and unlocking of the two elements 10 and 20 of the coupling.

This arm 24 includes, on its face situated opposite the base 21, three studs, respectively 27, 28 and 29, the first of which is arranged near the pin 25, and the other two of which are arranged near the free end 30 of this arm, and which are each accommodated in an oblong slot of matching shape, respectively 31, 32 and 33, formed in the base 21. The function of these studs 27, 28 and 29 is to maintain the arm 24 in a plane parallel to that of the base 21 during its pivoting and to ensure the guiding thereof, particularly by limiting the amplitude of this pivoting in this same plane between an unlocked position, which is that represented in FIGS. 2 and 4, and a locked position, which is that shown in FIG. 5. To do this, as can be seen in FIGS. 6 and 7, each of the studs 27, 28 and 29 has, at its free end, a bearing face, respectively 27a, 28a and 29a, sliding on a face, respectively 31a, 32a and 33a, arranged opposite on one of the walls of each of the oblong slots 31, 32 and 33. As is illustrated in FIGS. 6 and 7, the faces 27a, 28a, 29a, 31a, 32a and 33a are advantageously plane faces.

Furthermore, as can be seen in FIG. 5, the arm 24 has, still on its face situated opposite the base 21, and between the stud 29 and the free end 30 of this arm, a cylindrical stub 40 which is able to ensure its immobilization in the locked position after it has passed, in the direction of the arrow f, a nose 41 which is situated on the external edge of the base 21, at the end of a portion of this base shaped in an inward curve 42 in such a way as to facilitate the gripping of the said free end 30 of this arm.

As has been mentioned previously, the arm 24 also has, projecting from the middle part of its face situated opposite the joining piece 22, a rib 43 which, like the annular rib 14 of the joining piece 12, has two bevelled faces 43a and 43b, of which the face 43b matches the face 14b of this annular rib in such a way as to ensure, after engagement of the joining piece 22 in the joining piece 12 and positioning of the arm 24 in the locked position, the locking of the element 10 on the element 20 through cooperation with a portion of the same length as that of the said annular rib 14.

As can clearly be seen in FIG. 3, the cylindrical wall 23 of the joining piece 22 has, on its external face and in the area of its free end, a flange 44 which is substantially parallel to the base 21 and which extends radially in the direction of the external edge of this base (extension which has been accentuated for reasons of clarity in FIG. 3).

According to the invention, this flange 44, whose function is to axially retain the free end 19 of the annular lip 18 of the joining piece 12 when the joining pieces 12 and 22 are engaged, is not present around the entire circumference of the joining piece 22, but occupies a sector of this circumference corresponding to an angle substantially equal to 250° and whose midpoint 45 is situated diametrically opposite the middle of the rib 43 carried by the arm 24.

Moreover, this flange 44 is a diminishing flange whose width is at its maximum at the midpoint 45 of the circular sector which it occupies—and in the area of which this width is advantageously between 0.5 and 2 mm depending on the diameter of the joining piece 22 (which is itself advantageously between 25 and 100 mm)—and decreases progressively in the direction of the ends 46 and 47 of this sector.

As can be seen in FIGS. 3 and 8, the cylindrical wall 23 of the joining piece 22 additionally has, projecting from its external face, an annular bead 48 of substantially rectangular cross section. This annular bead is intended to serve, in the condition of use of the ostomy appliance, as an abutment for the bottom of the annular lip 18 of the joining piece 12 in such a way as to prevent the latter, under the effect of the weight of the bodily matter collected in the collecting bag, from crushing against the cylindrical wall 23 of the joining piece 22 and, on account of this crushing, the free end 19 of this lip moving away from this wall, thereby leading to loss of leaktightness, or even disengaging from the flange 44, thereby leading to disconnection of the bag and bag holder.

The functioning of this first embodiment of a coupling according to the invention results directly from the above. To join the elements 10 and 20 together, these two elements are brought opposite each other, after first ensuring that the arm 24 is in the unlocked position, and they are positioned in such a way as to bring the annular lip 18 carried by the joining piece 12 of the element 10 to bear on the flange 44 of the joining piece 22 of the element, in the area of the midpoint of this flange. The joining piece 22 is then engaged in the joining piece 12, by pivoting one element in relation to the other. Given the ability of the annular lip 18 to deform elastically, this engagement is effected practically without any application of pressure, and is so despite the fact that the free end 19 of this lip has, as has been previously mentioned, an internal diameter smaller than the external diameter of the cylindrical wall 23 of the joining piece 22 and, on a part of its circumference, has to get past the flange 44 carried by this wall before coming to bear against the external face of the latter. When the joining piece 22 is engaged fully in the joining piece 12, the arm 24 is then pivoted in the direction of the arrow f until the stub 40 moves past the nose 41 and finds itself immobilized by the latter, the effect of which is, as is illustrated in FIG. 8, to cause the rib 43 of this arm to penetrate into the portion of the annular groove 16 which is situated opposite it, in such a way that the bearing, upon this rib, of the portion of the annular rib 14 of the joining piece 12 which limits this groove portion counters any separation of the joining pieces 12 and 22.

Thus, in this condition, the attachment of the two elements 10 and 20 of the coupling is ensured, on the one hand, on that part of the circumference of the joining piece 22 where the flange 44 is present, via this flange which guarantees the mechanical immobilization of the free end 19 of the annular lip 18 of the joining piece 12 in the case where the latter might be caused to move axially (for example, in the condition of use of the ostomy appliance, under the effect of the weight of the matter collected in the collecting bag) and, on the other hand, on that part of the circumference of the joining piece 22 where the flange 44 is absent, via the rib 43 carried by the arm 24 which, by cooperation with a portion of the same length as that of the annular rib 14 of the joining piece 12, guarantees the locking of the said elements 10 and 20.

In this condition, however, it is possible to move one element of the coupling in relation to the other, not by extraction, but by rotation about its axis, especially in order to modify the position of the bag in relation to the bag holder in the condition of use of the ostomy appliance, and to do so without any risk of causing inadvertent separation of these elements.

To separate the two elements 10 and 20 of the coupling, it is necessary to release the stub 40 from the nose 41, to pivot the arm 24 in the direction opposite to that shown by the arrow f, which allows the rib 43 to be freed from the portion of the annular groove 16 of the joining piece 12 in which it was situated, and thereby to free that portion of the annular rib 14 with which it was cooperating, then to pull slightly on the base of one of the two elements, for example on the portion of base 11 of the element 10 situated opposite the inward curve 42 formed in the base 21 of the element 20, in such a way as to effect the disengagement of the joining pieces 12 and 22 in line with the rib 43. This disengagement is achieved without difficulty since, in the area of this rib, the joining piece 22 is without any flange capable of axially retaining the free end 19 of the annular lip 18 of the joining piece 12. It then suffices to pivot one element relative to the other in order to release the free end 19 of the annular lip 18 from the flange 44 and, in this way, to achieve the separation of the two elements of the coupling.

The functioning of this coupling is thus very simple and reliable and, for the purpose of joining the two elements of this coupling together, and also for disconnecting them, it requires only the application of extremely moderate forces (of pressure in the first instance, and of traction in the second).

Figure 2:
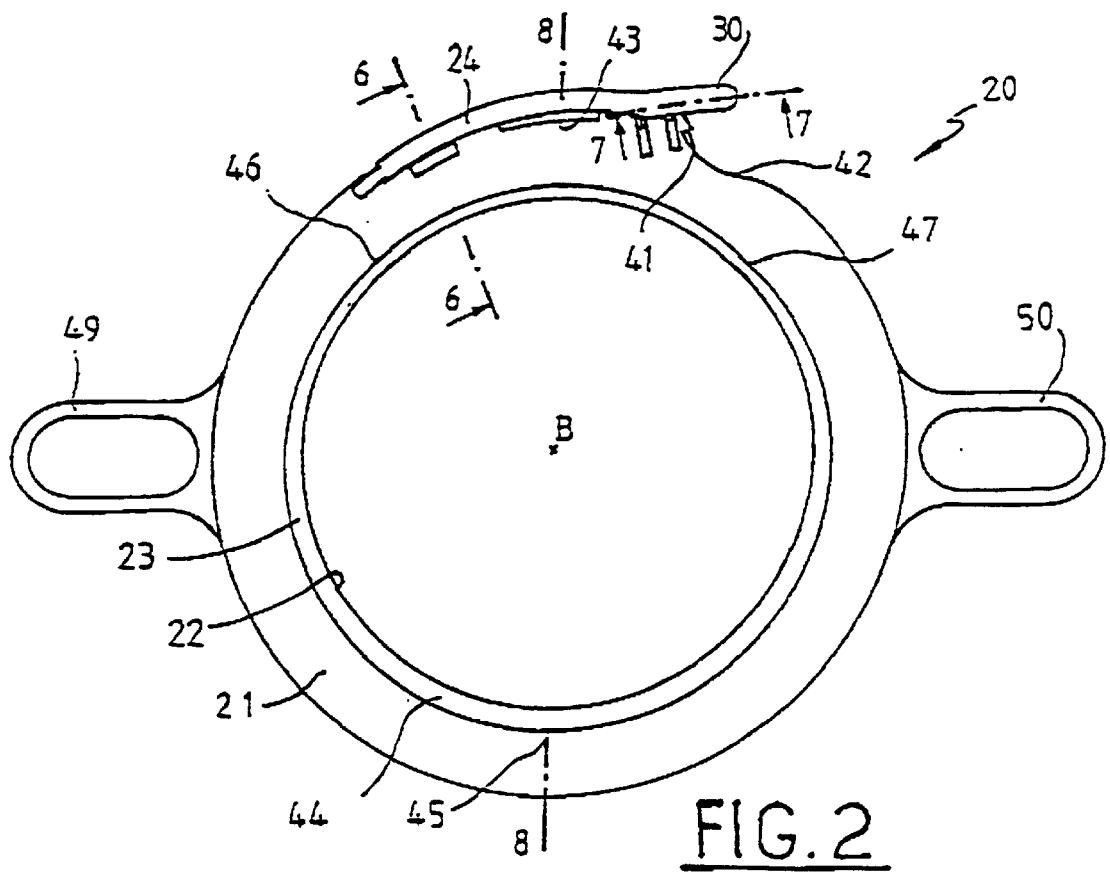
FIG. 2 is a plan view of the second element of a coupling for an ostomy appliance according to the invention, for this first embodiment of the coupling.

As has already been mentioned, the elements 10 and 20 of the embodiment of the coupling according to the invention which has just been described are intended to be fixed on the collecting bag and on the bag holder, respectively, of an ostomy appliance. This is the reason why two brackets 49 and 50 are provided on the external edge of the base 21 of the element 20, as can be seen in FIG. 2, which brackets 49 and 50 are diametrically opposite each other and project radially outwards from this base. These brackets are each provided with an orifice and, if the patient so desires, advantageously allow the securing of the bag holder on the area surrounding the stoma to be reinforced by means of a strap.

The element 10 can be fixed on the collecting bag by welding or adhesively bonding the base 11 of this element directly around the opening formed in one of the walls of this bag in order to allow the bodily matter evacuated via the stoma to flow into the said bag by way of the bag holder, while the element 20 is preferably fixed on the bag holder, in a manner known per se, by way of a circular collar (not represented in FIGS. 2 to 7) extending radially from the internal edge of the base 21 in the direction of the centre of the latter, this collar being fixed by welding, adhesive bonding or any other means on that face of the said bag holder opposite the one intended to be fixed on the patient's body, around the opening intended to encircle the stoma in the condition of use and in such a way that the arm 24 is placed in the upper area of this bag holder.

Alternatively, however, it is possible to provide an ostomy appliance in which, conversely, it would be the bag holder which would be equipped with the element 10 and the collecting bag which would comprise the element 20, so that in this case the brackets 49 and 50 would be present on the external edge of the base 11 of the element 10. It is of course also possible to provide an appliance in which neither the element 10 nor the element 20 would be equipped with brackets.

Figure 9:
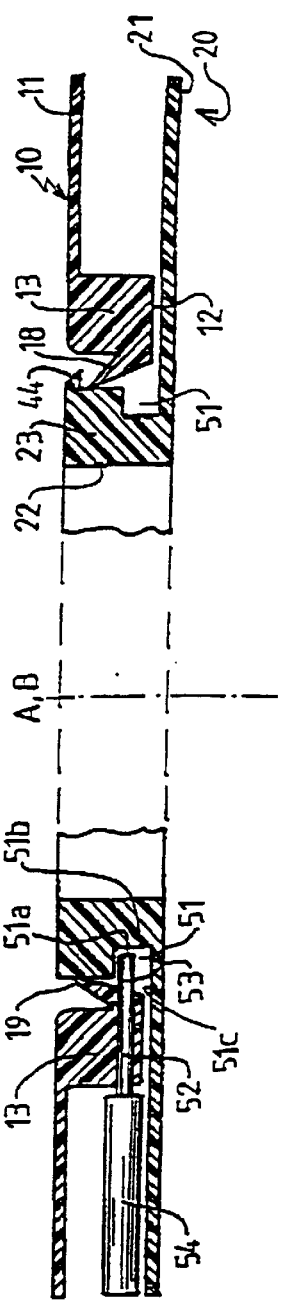
FIG. 9 is a diagrammatic cross section similar to that in FIG. 8, but for a second embodiment of a coupling for an ostomy appliance according to the invention.

FIG. 9 illustrates another embodiment of a coupling according to the invention in which the locking member and its control mechanism are joined to the first element 10, and not to the second element 20 of this coupling, as was the case in the previously described embodiment.

For this reason, in this embodiment, the cylindrical wall 13 of the joining piece 12 of the first element, although comprising, as in the previously described embodiment, an elastically deformable annular lip 18 projecting from its internal face and intended to ensure the leaktightness of the coupling with respect to the bodily matter collected in the condition of use of the ostomy appliance, is without any annular rib on its external face. By contrast, the cylindrical wall 23 of the joining piece 22 of the second element includes an annular groove 51 which extends radially in its thickness from its external face and which is delimited by three walls: a first wall 51a substantially parallel to the base 21, a second wall 51b substantially perpendicular to this base and constituting the bottom of this groove, and a third wall formed by the base 21 itself.

Furthermore, the cylindrical wall 13 of the joining piece 12 of the first element 10 is traversed, in the area of the base of the annular lip 18, by an advantageously tapped cylindrical opening 52 in which there is arranged a threaded cylindrical rod 53 which is shaped in such a way that its internal end—that is to say the end of this rod emerging from the cylindrical wall 23—is shaped in such a way as to be able to penetrate the annular groove 51 of the joining piece 22. The external end of the threaded rod 53—that is to say the end emerging from the external face of the cylindrical wall 13—is for its part equipped with a knurled wheel 54 which, after engagement of the joining piece 22 in the joining piece 12, is able to permit the displacement by rotation of the said rod in the opening 52 between an unlocked position and a locked position, which is that shown in FIG. 9 and in which its internal end is lodged in a portion of the annular groove 51 in such a way that the bearing of the threaded rod 53 on the portion of the wall 51a delimiting this groove portion counters any separation of the joining pieces 12 and 22.

Thus, as can be seen in FIG. 9, in this condition the securing of the two elements 10 and 20 of the coupling is ensured, on the one hand, on that part of the circumference of the joining piece 22 where the flange 44 is present, via this flange which guarantees the mechanical immobilization of the free end 19 of the annular lip 18 of the joining piece 12 in the case where the latter might be caused to move axially, and, on the other hand, on that part of the circumference of the joining piece 22 where the flange 44 is absent, via the internal end of the threaded rod 53 carried by the joining piece 12 which, by cooperation with a portion of the annular groove 51 of the joining piece 22, guarantees the locking of the said elements 10 and 20.

In this case too, it is possible to move one element of the coupling in rotation relative to the other one in order to modify the position of the bag in relation to the bag holder in the condition of use of the ostomy appliance. However, in this embodiment, it is advantageous to provide for the presence, on the base, of two stops which are able to limit the rotation of one element relative to the other on a predetermined angular sector when these elements are joined together, in such a way as to prevent the threaded rod 53 from being brought into cooperation with a portion of the annular groove 51 which would be situated in the angular sector occupied by the flange 44 of the joining piece 22, and an area thus being created in which the joining pieces 12 and 22 would at one and the same time be without means able to axially retain the end 19 of the annular lip 18 and means able to ensure the locking of the elements 10 and 20, and presenting an angular extension sufficient to cause inadvertent disconnection of these two elements.

Thus, in the case where the flange 44 occupies an angular sector of about 250°, these stops will advantageously be arranged on the base 21 of the element 20 in such a way as to limit the rotation of one element relative to the other on an angular sector of about 90°, of which the midpoint is diametrically opposite the midpoint 45 of the angular sector occupied by the said flange 44.

Irrespective of the embodiment of a coupling according to the invention, the elements 10 and 20 are advantageously made of a relatively rigid plastic (with a Shore D hardness preferably of between 40 and 86) of the type comprising polyethylene, polypropylene, thermoplastic polyester, polyamide or ABS copolymer not charged with a structural reinforcement.

As will be evident from the foregoing, the invention is not in any way limited to those embodiments which have just been more explicitly described; on the contrary, it encompasses all variants thereof which may occur to the person skilled in the art, without departing from the context or from the scope of the present invention. Thus, in particular, in order to ensure the locking of the two elements of the coupling, it is possible to use numerous other devices, both for the locking member and also for its activating mechanism, which may consist, for example, of a lever, a push-button or an articulated link mechanism.

What is claimed is:

1. A coupling for an ostomy appliance, comprising:
   first and second coupling members, each including a base defining a plane and equipped with a central opening, and a tubular joining piece surrounding said opening,
   the joining piece of the first member comprising, on an internal face, an elastically deformable annular lip whose free end is directed towards the plane of the base of said first member, and
   the joining piece of the second member including, on an external face, means for retaining axially the free end of said elastically deformable annular lip, and wherein said means occupies a part of the circumference of the tubular joining piece of the second coupling member, and guarantees, on that part of circumference, an axial retention of the free end of the annular lip of the first coupling member; and wherein
   said coupling further includes a locking member which is either in one piece with the first coupling member or in one piece with the second coupling member, but which in either case is located diametrically opposite the midpoint of the means for axial retention of the free end of the annular lip.

2. A coupling according to claim 1, wherein the element which comprises the locking member further comprises a control mechanism, and the locking member is intended to cooperate in response to the activation of said control mechanism, with a bearing surface which is formed on the joining piece of the other of the two elements of the coupling.

3. A coupling according to claim 1, wherein the locking member and the control mechanism are joined to the first element of this coupling, and the locking member is intended to cooperate with a bearing surface which extends radially inwards from the external face of the joining piece of the second element inwards from this joining piece.

4. A coupling according to claim 3, wherein the bearing surface intended to cooperate with the locking member is formed by a wall situated opposite the base of the second element, of a recess formed in the thickness of the joining piece of this second element.

5. A coupling according to claim 4, wherein the recess formed in the thickness of the joining piece of the second element extends over the entire circumference of the joining piece of the second element.

6. A coupling according to claim 5, wherein the base of the second element includes two stops for limiting the rotation of one element relative to the other when the two elements of the coupling are joined together.

7. A coupling according to claim 6, wherein the locking member is in one piece with the control mechanism and consists of a rod which is placed in a cylindrical opening passing through the joining piece of the first element, one end of which can be lodged in the recess formed in the thickness of the joining piece of the second element while the other end is integral with said control mechanism.

8. A coupling according to claim 7, wherein the rod is threaded over all or part of its length and the control mechanism is formed by a knurled wheel.

9. A coupling according to claim 6, wherein the control mechanism comprises an arm (24) which is mounted so as to pivot about an axis formed by a pin (25) with which it is provided, and which is engaged in an orifice (26) formed in the base of the second element.

10. A coupling according to claim 9, wherein the second element comprises means for maintaining and guiding said arm in a plane parallel to the plane of the base of the second element.

11. A coupling according to claim 10, wherein the means for maintaining and guiding the arm comprise at least one stud projecting from a face of said arm situated opposite the base of the second element, having a free return end which determines a bearing face and which is adapted to pass through an oblong slot formed in the base of the second element, so that said bearing face slides on a face of the base of the second element situated on the side opposite said arm.

12. A coupling according to claim 11, wherein said arm includes, on its face situated opposite the base of the second element, at least one projecting piece adapted to cooperate with a nose formed on an external edge of the base of the second element in order to ensure immobilization of the locking member in the locked condition.

13. A coupling according to claim 2, wherein the locking member and the control mechanism are joined to the second element, and the locking member is intended to cooperate with a bearing surface which extends radially outwards from an external face of the joining piece of the first element outwards from this joining piece.

14. A coupling according to claim 13, characterized in that the rib with bevelled faces projecting from the external face of the joining piece of the first element extends over the entire circumference of this joining piece.

15. A coupling according to claim 14, wherein the locking member is in one piece with the control mechanism and consists of at least one rib with bevelled faces, of which one of the faces matches the face of the rib of the joining piece of the first element intended to serve as a bearing surface, and which projects from the face of the said control mechanism situated opposite the joining piece of the second element.

16. A coupling according to claim 13, wherein the bearing surface intended to cooperate with the locking member is formed by a face, situated opposite the base of the first element, of a rib with bevelled faces projecting from the external face of the joining piece of this first element.

17. A coupling according to claim 1, wherein the means for retaining axially the free end of the elastically deformable annular lip occupy a sector of the circumference of the joining piece of the second element corresponding to an angle of between about 180 and 320°.

18. A coupling according to claim 17, wherein the means for retaining axially the free end of the elastically deformable annular lip consist of a flange having a width and extending radially outwards from the external face of the joining piece of the second element outwards from this joining piece.

19. A coupling according to claim 18, wherein the flange is a diminishing flange whose width is at its maximum at the midpoint of the sector which it occupies and decreases progressively from said midpoint, said midpoint being diametrically opposite to the locking member.

20. A coupling according to claim 1, comprising means for immobilizing the locking member in the locked condition.

21. A coupling according to claim 1, wherein the second element of the coupling further includes means for limiting the radial displacement of the bottom of the elastically deformable annular lip in the direction of the joining piece of the first element when the two elements of the coupling are joined together.

* * * * *

UNITED STATES PATENT AND TRADEMARK OFFICE
CERTIFICATE OF CORRECTION

PATENT NO. : 6,409,710 B1
DATED : June 25, 2002
INVENTOR(S) : Holtermann

It is certified that error appears in the above-identified patent and that said Letters Patent is hereby corrected as shown below:

Column 11,
Line 36, "claim 1" should read -- claim 2 --;
Line 41, delete "inwards from this joining piece";
Line 63, "claim 6" should read -- claim 2 --;
Line 64, delete "(24)";
Line 65, delete "(25)";
Line 66, delete "(26)".

Column 12,
Line 24, delete "outwards from this joining piece";
Line 25, "characterized in that" should read -- wherein --;
Lines 51-52, delete "outwards from this joining piece".

Signed and Sealed this

Twenty-first Day of January, 2003

JAMES E. ROGAN
*Director of the United States Patent and Trademark Office*